United States Patent
Brogden et al.

(10) Patent No.: US 9,107,856 B2
(45) Date of Patent: Aug. 18, 2015

(54) DENTAL APPLIANCE CLEANSER

(75) Inventors: Kyle N Brogden, Parsippany, NJ (US); Stanley J. Lech, Parsippany, NJ (US); Naresh I. Mehta, Parsippany, NJ (US); Philip J. Oths, Parsippany, NJ (US)

(73) Assignee: GlaxoSmithKline, LLC, Wilmington, DE (US)

( * ) Notice: Subject to any disclaimer, the term of this patent is extended or adjusted under 35 U.S.C. 154(b) by 733 days.

(21) Appl. No.: 12/293,980

(22) PCT Filed: Mar. 22, 2007

(86) PCT No.: PCT/US2007/064596
§ 371 (c)(1), (2), (4) Date: Sep. 22, 2008

(87) PCT Pub. No.: WO2007/112250
PCT Pub. Date: Oct. 4, 2007

(65) Prior Publication Data
US 2009/0130032 A1    May 21, 2009

Related U.S. Application Data

(60) Provisional application No. 60/785,313, filed on Mar. 23, 2006.

(51) Int. Cl.
*A61K 8/00* (2006.01)
*A61K 8/92* (2006.01)
*A61Q 11/02* (2006.01)

(52) U.S. Cl.
CPC .................. *A61K 8/922* (2013.01); *A61K 8/925* (2013.01); *A61Q 11/02* (2013.01)

(58) Field of Classification Search
USPC .......................................................... 424/49
See application file for complete search history.

(56) References Cited

U.S. PATENT DOCUMENTS

| | | | |
|---|---|---|---|
| 3,808,686 A | 5/1974 | Tauman et al. | |
| 3,822,212 A | 7/1974 | Bryant et al. | |
| 4,317,788 A | 3/1982 | Imada et al. | |
| 4,511,486 A | 4/1985 | Shah | |
| 6,156,721 A | 12/2000 | Kwetkat et al. | |
| 6,506,803 B1 * | 1/2003 | Baker et al. | 424/678 |
| 2004/0247647 A1 * | 12/2004 | Ivory et al. | 424/440 |
| 2005/0265948 A1 | 12/2005 | Ridley et al. | |

FOREIGN PATENT DOCUMENTS

| | | |
|---|---|---|
| EP | 0 208 009 B1 | 1/1987 |
| JP | A-06-179895 | 6/1994 |
| WO | WO97/07821 | 3/1997 |
| WO | WO97/40124 | 10/1997 |
| WO | WO 9938481 A1 * | 8/1999 |

OTHER PUBLICATIONS

University Library, University of Michigan, Contact Angle (Liquid phase) http://www.lib.umich.edu/dentlib/Dental_tables/Contangle.html.

Panizza et al., "Controlled production of hierarchically organized large emulsions and particles using assemblies on line of co-axial flow devices," *Colloids and Surfaces A:Physiochemical and Engineering Aspects* (Jun. 2007) 312(1):24-31.

* cited by examiner

*Primary Examiner* — Dennis J Parad
(74) *Attorney, Agent, or Firm* — Nora L. Stein; Theodore R. Furman

(57) ABSTRACT

This invention relates to a dental appliance cleanser which is a metastable emulsion comprising about 50-99% w/w of an aqueous phase, about 1-50% w/w of a water immiscible oily phase, the oily phase having a combination of a one or more immiscible oils and one or more flavor oils. The dental appliance cleanser is applied to the dental appliance, outside the wearer's mouth, in the form of an aerated foam.

6 Claims, No Drawings

DENTAL APPLIANCE CLEANSER

This application is a 371 National Phase entry of international application number PCT/US2007/064596, filed Mar. 22, 2007, claiming priority from U.S. Application No. 60/785,313, filed Mar. 23, 2006.

FIELD OF THE INVENTION

This invention relates to a dental appliance cleanser which is a metastable emulsion comprising about 50-99% w/w of an aqueous phase, about 1-50% w/w of a water immiscible oily phase, the oily phase having a combination of a one or more immiscible oils and one or more flavor oils. The dental appliance cleanser is applied to the dental appliances, outside the wearer's mouth, in the form of an aerated foam.

BACKGROUND OF THE INVENTION

Full or partial dentures are intended to be worn in the mouth to replace missing teeth. Like teeth, dentures should be cleaned regularly to maintain good oral health. Like teeth, dentures should also be cleaned regularly for cosmetic reasons, for example to maintain fresh breath.

Unlike teeth, dentures can be removed for cleaning. Dentures are also made of durable materials, such as acrylic polymers, that can withstand relatively harsh cleaning conditions. As a result, dentures can be, and sometimes are, exposed to harsh cleaning conditions. Dentures are typically cleaned in one of two ways, either the dentures are soaked for some time in a cleansing bath or dentures are brushed with dentifrices or specially formulated cleansing creams.

Brushing with creams has the advantage of supplementing the cleaning formulation with mechanical action. Unfortunately, as with teeth, spots on the dentures can be missed or overlooked during the brushing process. As a result, the denture material can degrade over time, and remaining teeth and gums of the user may be exposed to disease agents and undesirable cosmetic consequences.

Soaking in a cleansing bath offers the advantage of reaching every part of a denture for cleaning. Full immersion of the denture in the bath allows the cleansing composition to reach areas that can not be reached by ordinary brushing with creams. Cleansing baths are not usually sold as such. Typically, the active ingredients are sold in solid form, as a denture cleanser powder or tablet, or in concentrated liquid form. The active ingredients are then dissolved in a water bath to form the cleansing bath.

Unfortunately, soaking surrenders the advantage of mechanical scrubbing found with creams and dentifrices. To compensate for this loss of mechanical cleaning, denture cleansing tablets and powders usually contain an effervescent system and strong chemical cleaning agents. Strong chemical cleaning agents, such as bleaches, can impart an unpleasant taste or odor to soaked dentures, however. Thus, denture cleanser manufacturers face a trade off between efficacy and cosmetic and organoleptic considerations.

Sprayable denture cleansers are described in U.S. Pat. Nos. 3,808,686 and 3,822,212. U.S. Pat. No. 4,511,486, issued Apr. 16, 1985, to Shah, discloses a foamable liquid denture cleanser comprising a surfactant, humectant, water and an appreciable amount of ethanol or isopropanol. The alcohol is used as a solubilizer for various excipients, as a component which imparts a fresh-tasting feel to the cleansed denture and to provide an antibacterial effect.

None of these methods provide for prolonged breath freshening, in particular for denture wearers. Denture wearers complain that their dentures give off an unpleasant odor, often called "denture breath". Products currently on the market require prolonged cleaning times, such as with soaking, without providing prolonged benefits such as a fresh mouth-taste and fresh breath. In many cases denture wearers must resort to brushing their dentures with regular toothpaste to keep dentures/breath fresh which can lead to scratching of the denture surface due to the abrasivity of toothpaste. In addition, since these methods do not provide for prolonged fresh breath, the denture wearer often resorts to cleaning the dentures multiple times per day which is inconvenient and stigmatizing.

Finding a denture cleanser that is applied easily and does not require extended cleansing times while maintaining prolonged fresh breath is an ongoing task. Acceptable agents must be non-toxic, non-staining, non-abrasive and water dispersible. In addition, the cleanser should be easy to dispense and apply to the dentures, and provide a clean denture in as few steps as possible. Maintaining prolonged fresh breath effects without having to clean the dentures multiple times per day is extremely desirable. Such a cleanser would be useful for other dental appliance wearers.

SUMMARY OF THE INVENTION

In one aspect, this invention relates to a dental appliance cleansing formulation substantially free of antimicrobial agents and dispensed in the form of an aerated foam, which is a metastable emulsion comprising about 50-97% w/w of an aqueous phase, about 2-50% w/w of a water immiscible oily phase, the oily phase having a combination of one or more immiscible oils and one or more flavor oils.

In another aspect, this invention relates to a method of cleansing a dental appliance outside the oral cavity comprising maintaining the dental appliance in contact with an aerated foam composition substantially free of antimicrobial agents for a dental appliance cleansing effective time, said aerated foam composition comprising about 50-99% w/w of an aqueous phase, about 1-50% w/w of a water immiscible oily phase, the oily phase having a combination of one or more immiscible oils and one or more flavor oils for a time sufficient to clean the dental appliance and rinsing the dental appliance with water.

In still another aspect, this invention relates to a dental appliance cleansing formulation substantially free of antimicrobial agents and or alcohol dispensed in the form of an aerated foam, which is a metastable emulsion comprising about 50-99% w/w of an aqueous phase, about 1-50% w/w of a water immiscible oily phase, and about 0.5-6% w/w of a surfactant selected from an anionic surfactant, a zwitterionic surfactant and a non-ionic surfactant, or combination thereof, wherein the oily phase has a combination of one or more immiscible oils and one or more flavor oils.

In yet another aspect, this invention relates to a kit for delivering a dental appliance cleansing formulation substantially free of antimicrobial agents and dispensed in the form of an aerated foam, which is a metastable emulsion comprising about 50-99% w/w of an aqueous phase, about 1-50% w/w of a water immiscible oily phase, the oily phase having a combination of one or more immiscible oils and one or more flavor oils, the kit comprising a dispenser capable of dispensing a foam and a separately packaged volume of the dental appliance cleansing formulation.

In still yet another aspect, this invention relates to a method for maintaining prolonged fresh breath in the mouth of a dental appliance wearer by cleansing the dental appliance with a dental appliance cleansing formulation substantially free of antimicrobial agents and dispensed in the form of an aerated foam, which is a metastable emulsion comprising about 50-99% w/w of an aqueous phase, about 1-50% w/w of a water immiscible oily phase, the oily phase having a combination of one or more immiscible oils and one or more flavor oils, said cleansing comprising maintaining the dental appliance in contact with the dental appliance cleansing formulation for a time sufficient to maintain prolonged fresh breath, rinsing the dental appliance with water and placing the dental appliance in the mouth of the wearer.

DETAILED DESCRIPTION OF THE INVENTION

The terms "clean", "cleansing" or "cleaning" are used interchangeably herein to refer to removing food particles, stain and other oral debris by the mechanical action of brushing plus the breath freshening function of the inventive formulation.

The term "dental appliance" is used herein to refer to dentures or partial dentures, artificial teeth, removable orthodontic bridges and denture plates, both upper and lower types, orthodontic retainers and appliances, protective mouthguards, nightguards to prevent bruxism and/or Temporomandibular joint (TMJ) disorder, and the like.

The term "denture cleanser" is used herein to refer to a formulation for use outside the mouth to clean dental appliances.

The term "foamable formulation" is used herein to refer to a metastable liquid emulsion capable of being delivered from a dispenser using a propellant or a propellantless dispenser in the form of a foam.

The term "HLB" is used herein to refer to hydrophile/lipophile balance, a measure of the relative hydrophilicity/lipophilicity of surfactant molecules.

The term "immiscible oil" is used herein to refer to substances of the same phase or state of matter that cannot be uniformly mixed or blended. The term "metastable emulsion" is used herein to refer to a short-lived oil in water dispersion which will start to separate, if left undisturbed, in under 5 minutes.

The term "prolonged fresh breath" is used herein to refer to a combination of mouth-feel, denture odor control and mouth odor control sustainable for 2 or more hours.

Along with superior cleansing the other major benefit that this formulation provides is improved breath and a fresh mouth-taste which, tests in denture wearers have shown, lasts up to 5 hours. Therefore, this invention describes a foaming denture cleanser which is designed to clean dentures, kill bacteria, impart a fresh taste and freshen breath up to 5 hours.

The dental appliance cleanser formulation utilizes a metastable oil/water emulsion, in which the majority of the oil phase is composed of flavor and immiscible oils, including vegetable and/or mineral oils, with an aqueous phase consisting primarily of detergents, emulsifiers, a stain remover, a bacteriostatic agent, a flavor carrier, a sweetener, and buffering agents. The emulsion can be transiently formed and the product made homogenous by gentle shaking of the container prior to application.

The formulation is a liquid in a container which is activated to a foam via a foaming applicator head, either using a propellant or without a propellant. The formulation is designed to be applied directly to the dental appliance and recommended to be brushed on with a toothbrush or denture brush for a dental appliance cleansing effective time which is at least between about 30 and 60 seconds. In one embodiment, the dental appliance cleansing effective time is at least about 60 seconds. After cleaning, the formulation is rinsed-off the dental appliance with water and then placed in the mouth.

Surfactants and stain removers in the foam clean and penetrate the dental appliance, especially while being brushed-on. After at least between about 30 and 60 seconds, and then upon rinsing, the oil phase becomes unstable with the oil droplets coalescing. Without being bound to any particular theory, it is hypothesized that the formulation deposits on the surface of the dental appliance also carrying the flavors. Because the flavors are now in intimate contact with the dental appliance surface, they are better able to be adsorbed into the dental appliance structure. This phenomenon creates a noticeable pleasant mouth-taste and prolonged breath freshening even after rinsing. Prolonged fresh breath is achieved when the dental appliance is in contact with the cleansing formulation for at least about 30 to 60 seconds. In one embodiment, the dental appliance is in contact with the cleansing formulation for at least about 60 seconds in order to maintain prolonged fresh breath.

One particularly advantageous aspect of this invention is the fact that the dental appliance cleansing emulsion formulation contains between about 2 and 50% weight/weight ("w/w") of an oily phase yet can still be dispensed as an aerated foam. Indeed, one skilled in the art would not expect a metastable emulsion with such a high oil content to dispense as an aerated foam.

Suitable immiscible oils for use in the instant invention include, but are not limited to, sesame oil, soybean oil, canola oil, coconut oil, fractionated coconut oil, fish oil or, mineral oil. One embodiment of this invention contains sesame oil. The immiscible oil is contained in the formulation in an amount between about 0.5-20% w/w. One embodiment of this invention contains an immiscible oil in an amount between about 1-8% w/w. Another embodiment of this invention contains sesame oil in an amount between about 3-6% w/w.

In addition to an immiscible oil, the denture cleansing formulation contains flavor oils in an amount between about 0.5-15% w/w. Suitable flavor oils for use in the instant invention include, but are not limited to, essential oils, such as spearmint, wintergreen, limonine, menthol, peppermint, linolol, citrus oils, anethole, fennel sweet, eucalyptol, camomile oil, basil oil, ginger, rosemary oil, menthol laevo, methyl salicylate, clove bud oil, tarragon, tea tree oil, thymol, cardamom oil, citral, origanumDamascone F, decanol, nonanol, decanal, ionone alpha, vanillin, aniseed, cinnamic aldehyde, lime or mixtures thereof. One embodiment of this invention contains a flavor oil in an amount between about 2-6% w/w.

The aqueous phase of the metastable emulsion is present in the formulation in an amount between about 50 and 99% w/w. One embodiment of this invention contains water in an amount between about 50-80% w/w. A second embodiment of this invention contains water in an amount between about 75-90% w/w.

In order to achieve significant foaming, a surfactant is added to the denture cleansing formulation and acts as a foam producing agent, and assists with the ability of the formulation to clean effectively.

Suitable surfactants for use in the invention include, but are not limited to, anionic surfactants, zwitterionic surfactants and non-ionic surfactants, or a combination thereof. Suitable anionic surfactants include, but are not limited to, sodium lauryl sulphate and other alkyl sulfates, alkyl ethersulfates, sodium lauryl sulfoacetate, dialkyl sulfosuccinates, alkylbenzene sulfonates, alpha olefin sulfonates, acyl N-methyl taurates and, sodium lauroyl sarcosinate. One embodiment of the invention contains sodium lauryl sulphate, in an amount of 0.5-4% w/w.

Suitable non-ionic surfactants include, but are not limited to, polyoxyl hydrogenated castor oil, the ethoxylated sorbitan alkanoates, fatty acid ethoxylates, fatty alcohol ethoxylates, fatty amine ethoxylates, polyethylene oxide/polypropylene oxide block polymers (Pluronics) and sucrose esters. One embodiment of the invention contains polyoxyl 40 hydrogenated castor oil, in an amount of 0.5-6% w/w.

Suitable zwitterionic surfactants include, but are not limited to, cocamidopropyl betaine and alkyl amidopropyl betaines. One embodiment of the invention contains cocamidopropyl betaine, in an amount of 0.5-4% w/w. One embodiment of this invention contains a surfactant mixture of 0.5-4% w/w sodium lauryl sulphate, 0.5-6% w/w polyoxyl 40 hydrogenated castor oil, and 0.5-4% w/w cocamidopropyl betaine.

Suitable surfactants, including mixtures of surfactants, for use in this invention have an HLB greater than about 10. In one embodiment, the HLB of the surfactant or mixtures thereof, is greater than about 16.

The presence of a humectant helps retain moisture. Suitable water soluble pharmaceutically acceptable humectants include, but are not limited to glycerin, sorbitol (generally employed as a 70% solution), zylitol, mannitol, and galactitol. One embodiment of this invention contains a humectant in an amount between about 1-20% w/w. Another embodiment of the invention contains a humectant in an amount between about 5-15% w/w.

Excipients may also be added to the instant denture cleansing formulation—excipients such as preservatives, e.g., sodium benzoate, benzoic acid, methylparaben, propylparaben, and the like; sequesterants, e.g., edentate disodium, citrates, tartrates, sodium metasilicate, sodium pyrophosphates, potassium pyrophosphates, tripolypyrophosphates, sodium tripolypyrophosphates; anti-oxidants, e.g., BHT (butylated hydroxytoluene), BHA (butylated hydroxyanisole) and tert-butylhydroquinone; buffering agents; stain removers, e.g., polyethylene glycol; coloring agents; viscosity modifiers; and mixtures thereof.

The compositions according to the present invention may be prepared by admixing the ingredients in the appropriate relative amounts in any order that is convenient (see, Example 1 below).

The dental appliance cleansing foams are easily dispensed from readily available foam-producing devices known in the art. Either propellantless dispensers or dispensers using a propellant are suitable for use with this inventive formulation. Examples are the F2 Finger Pump Foamer or the M3 Mini-finger Pump Foamer manufactured by Airspray (Pompano Beach, Fla.) or the 37MS Portable Anti-clog Pump manufactured by Emsar (Alkmaar, The Netherlands).

The dental appliance cleanser formulation is placed on the dental appliance for a time sufficient to cleanse the dental appliances. Once the foam is applied it is recommended that the dental appliance wearer brush the dental appliance with a toothbrush or a denture brush, although this is not required. After a minimum of 60 seconds, the denture can be rinsed with water and replaced in the mouth.

Another aspect of this formulation is its effectiveness in killing bacteria and other microbial organisms associated with denture odor, without having a specific antimicrobial agent in the formulation. Microbiological kinetic kill studies were used to evaluate the anti-microbial efficacy of such a liquid-to-foam denture cleanser prototype at 90 seconds of contact time to bacteria.

The study focused on the effectiveness of the denture cleansing formulation described herein against oral malodor causing bacteria such as *Fusobacterium nucleatum*, *Klebsiella pneumoniae*, *Streptococcus sanguis*, *Actinomyces viscosus* and *Veillonella* spp. Table 1 shows the results as the percentage of bacteria that have been killed in suspension at 90 seconds of contact time with diluted product, the product being a formulation falling within the scope of this invention. The kill kinetic model evaluated the product at a 1:1 dilution ratio in a suspending solution of sterile city water, sterile artificial saliva and other interfering substances, such as, Bovine Serum Albumin. This model approximates its dilution factor as it mixes with residual saliva, water, and other materials on the denture base. The model represents the likely conditions that the product may encounter on the dentures.

Test Protocol:

Cultures of the organisms tested were started in Tryptic Soy Broth for facultative organisms (e.g., *Klebsiella pneumoniae* and *S. sanguis*) and Fluid Thioglycollate Medium with 2% Oxyrase for Broth for anaerobic organisms (e.g., *Fusobacterium nucleatum* and *Veillonella* spp.). The facultative organisms were incubated for a minimum of 48 hours and the anaerobes for a minimum of 72 hours at 30°-35° C. Use of a T3 to T5 culture is recommended.

A control tube containing 2.4 mL of Sterile Incoming City Water ("SICW"), 2.2 mL Artificial Saliva ("AS"), and 0.2 mL of Bovine Serum Albumin ("BSA") was inoculated with 0.2 mL of the test organism. This step was repeated for each test organism separately. A 1 mL aliquot was removed from each of the control tubes and a 10-fold serial dilution in Dey/Engley Neutralizing Broth was made. From the serial dilutions, 2×1 mL aliquots were taken from dilutions 4 through 6. 20-25 mL of Tryptic Soy Agar was added to dilution aliquots of the facultative organisms. 20-25 mL Schaedler Agar w/10% Oxyrase for Agar was added to the dilution aliquots for the anaerobic organisms. After the agar solidified, approximately 5 mL overlay of Schaedler Agar was added to the plates containing the anaerobic organisms.

A second set of tubes was inoculated with 0.2 mL of the test organisms; the second set of tubes containing 1.1 mL of SICW, 1.0 mL of AS and 0.2 mL BSA. 2.5 mL of the inventive formulation described in Example 2 below, was added to each of the second tubes ("the test solution"). After 90 seconds and 120 seconds (+/−5 secs at each time point), 1.0 mL aliquots of each of the test solutions was removed from each of the test solution tubes and a 10-fold serial dilution in Dey/Engley Neutralizing Broth was made. Light agitation by vortexing was performed in between sampling points. Serial dilutions were taken out to a dilution factor of $10^{-4}$. Duplicate 1.0 mL aliquots from each dilution were plated to 150 mm Petri dishes. The facultative organisms were incubated for a minimum of 48 hours and the anaerobes for a minimum of 72 hours at 30°-35° C. After incubation, the colony-forming units ("CFU's") were determined, an average taken and the average was multiplied by the dilution factor. The $\log_{10}$ was taken (two decimal places) of this value. Testing of all organisms was run in duplicate.

The percent reduction at the 90 second time-point was calculated as follows: the dilutions where the CFU-count was between 10-100 CFU's were used to determine the log value at the 90-second time point for each organism. The results reported in Table 1 below, are recorded as percent reduction calculated by the following formula (a−b)/a×100 wherein, variable "a" is the antilog of the number of inoculated organisms in the control solution; and variable "b" is the antilog of the number of organisms surviving in the test solution. Variables "a" and "b" will be the average log values for each organism taken at the 90-second time-point for all test replicate runs.

TABLE 1

| Organism | Control Log | Time-Point Log Values 90 secs | Log Reduction Values 90 secs | % Reduction @ 90 secs |
|---|---|---|---|---|
| *Klebsiella pneumoniae* | | | | |
| RT | 7.62 | 2.81 | 4.81 | >99.99 |
| 2 mo @40/75 | 7.62 | 2.95 | 4.67 | >99.99 |
| *Fusobacterium nucleatum* | | | | |
| RT | 4.98 | <1.00 | >3.97 | 99.99 |
| 2 mo @40/75 | 4.98 | 1.24 | 3.74 | 99.98 |
| *Veillonella atypical* | | | | |
| RT | 7.52 | <1.00 | >6.52 | >99.99 |
| 2 mo @40/75 | 7.52 | <1.00 | >6.52 | >99.99 |
| *Actinomyces viscosus* | | | | |
| RT | 6.51 | <1.00 | >5.51 | >99.99 |
| 2 mo @40/75 | 6.51 | <1.00 | >5.51 | >99.99 |
| *Streptococcus sanguis* | | | | |
| RT | 6.12 | <1.00 | >5.12 | >99.99 |
| 2 mo @40/75 | 6.12 | <1.00 | >5.12 | >99.99 |

As used in Table 1, the term "RT" refers to room temperature, and the term "2 mo @40/75" refers to predictive accelerated stability conditions for 2 months at 40° C. and a relative humidity of 75%.

Another unique aspect of this dental appliance cleansing formulation is its low interfacial surface tension and, especially the unusually low contact angle which it forms on dental acrylic. Liquid/surface contact angles and surface tensions are indicative of how well a formulation spreads, wets and ultimately penetrates a surface—with lower contact angles and surface tensions indicating better wetting/spreading and penetration. Formulations with lower contact angles and surface tensions are better able to penetrate into pores to help remove dirt from inside the pore structure. Current liquid dental appliance cleaners have acrylic contact angles greater than 25°. The formulations described herein have acrylic contact angles of less than 24°, with most between 5° and 18°. The extremely low acrylic contact angles are thought to be achieved by a combination of the surfactant system, benzoic acid, pH and the presence of the oil.

Again, without being bound by any particular theory, the pH of these formulae, along with the presence of an organic acid (e.g., benzoic acid, sorbic acid, malic acid, citric acid, salicylic acid and propionic acid (also known as propanoic acid)) is thought to further reduce the contact angle on dental acrylic, with formulae pH's between 2.5 and 5.5. The pH of the dental appliance cleansing formulation is suitably between about 4.0 and 5.5. One embodiment of the inventive formulation has a pH of 4.8. A lower pH is also believed to optimize the activity of the preservatives, improve active antimicrobial effectiveness and, assist in flavor retention (by lowering the contact angle of the formula) and therefore, in enhancing fresh breath.

Contact angle data on dental acrylic, using formulae with and without benzoic acid/benzoate and oil phase, are shown in Table 2, below. The pH of formulations 1-4, shown below, was adjusted to pH between 4.8 and 5.0. Formulation 5 is formulation '1' ('full formula') adjusted to pH 7.5 with a 3N sodium hydroxide solution.

TABLE 2

| Drop # | Formulation '1' With Benzoic Acid/Benzoate, With Oils ('Full Formula') | Formulation '2' With Benzoic Acid/Benzoate Without Oils | Formulation '3' Without Benzoic Acid/Benzoate With Oils | Formulation '4' Without Benzoic Acid/Benzoate, Without Oils | Formulation '5' Formulation '1' with pH at 7.5 |
|---|---|---|---|---|---|
| 1 | 8.4 | 21.3 | 27.2 | 39.4 | 26.5 |
| 2 | 7.9 | 20.5 | 26.6 | 40.8 | 25.8 |
| 3 | 9.4 | 21.5 | 28.3 | 39.3 | 26.7 |
| 4 | 9.4 | 20.9 | 26.6 | 39.9 | 26.5 |
| 5 | 8.5 | 21.2 | 27.4 | 40.3 | 26.4 |
| 6 | 7.9 | 21.2 | 27.5 | 40.2 | 26.3 |
| 7 | 7.7 | 21.2 | 28.1 | 39.8 | 26.7 |
| 8 | 7.9 | 20.0 | 28.1 | 40.2 | 26.6 |
| 9 | 9.4 | 20.9 | 28.1 | 39.6 | 26.5 |
| 10 | 8.0 | 20.1 | 27.5 | 40.7 | 26.1 |
| Average | 8.5 | 20.9 | 27.5 | 40.0 | 26.4 |
| Std. Dev. | 0.7 | 0.5 | 0.6 | 0.5 | 0.3 |

The data in table 2 show that low acrylic contact angles are achieved by formulations containing benzoic acid at pH 4.8-5.0, along with the presence of an oil phase. All of these factors together, are believed to contribute to a desired low contact angle, in the case of Formulation '1', of 8.5°. When the pH of Formulation '1' is increased from 4.9 to 7.5 (Formulation '5'), the contact angle on acrylic increases from 8.5° to 26.4°.

Dental appliance cleansing formulations falling within the scope of this invention are more particularly illustrated in conjunction with the following non-limiting examples.

EXAMPLES

Example 1

To Make 3.000 Kilograms of Product

In a suitable container, equipped with a propeller-type mixer, 2,101.2 g of Purified Water, USP was added and then 210.0 g Glycerin 99.7%, USP was added. The contents were mixed 'medium' speed. While this mixture continued to be mixed the following ingredients were added, making sure that each ingredient was fully dispersed/dissolved before adding the next: 120.0 g Sorbitol 70% Solution, USP; 15.00 g Polyethylene Glycol 400, NF; 30.00 g Sodium Benzoate, NF; 15.00 g Cocamidopropyl Betaine; 45.00 g Sodium Lauryl Sulphate, NF; 1.500 g Edetate Disodium, USP; 60.00 g Polyoxyl 40 Hydrogenated Castor Oil, USP; 90.00 g Gantrez Acid S97 BF (13% solution); 12.00 g Sodium Saccharin, USP; 150.0 g Sesame Oil, NF; 135.0 g Flavor, 0.300 g Butylated Hydroxytoluene, NF; and 15.00 g Benzoic Acid, NF.

After the last ingredient was dissolved, the mixer was placed on 'high', making sure that the propeller mixer was creating a vortex to the dispersion. Mixing was continued, covered, for 40-50 minutes. The specific gravity of the final de-aerated dispersion was 1.032.

Example 2

The following Table lists the ingredients for a suitable formulation falling within the scope of this invention.

| Ingredient Name | % w/w |
|---|---|
| Purified Water (USP - Water*) | 70.040 |
| Glycerin (99.7%), USP | 7.000 |
| Sorbitol Solution 70%, USP | 4.000 |
| Polyethylene glycol 400 (PEG 400) | 0.500 |
| Sodium Benzoate, NF | 1.000 |
| Polyoxyl 40 Hydrogenated castor Oil, USP | 2.000 |
| Cocamidopropyl Betaine | 0.500 |
| Edetate Disodium, USP | 0.050 |
| Butylated Hydroxytoluene, NF | 0.010 |
| Sodium Saccharin, USP | 0.400 |
| Sodium Lauryl Sulfate, NF | 1.500 |
| Gantrez Acid S-97 BF, 13% Solution | 3.000 |
| Flavor | 4.500 |
| Sesame Oil, NF | 5.000 |
| Benzoic Acid, NF | 0.500 |
| TOTAL | 100.000 |

The above description fully discloses the invention including preferred embodiments thereof. Modifications and improvements of the embodiments specifically disclosed herein are within the scope of the following claims. Without further elaboration it is believed that one skilled in the art can, given the preceding description, utilize the present invention to its fullest extent. Therefore any examples are to be construed as merely illustrative and not a limitation on the scope of the present invention in any way. The embodiments of the invention in which an exclusive property or privilege is claimed are defined as follows.

What is claimed is:

1. An alcohol-free dental appliance cleansing formulation which is applied to the dental appliance outside the wearers mouth for at least about 60 seconds, and which is a metastable emulsion comprising about 75-90% w/w of an aqueous phase, about 0.5-20% w/w of a water immiscible oily phase, the oily phase having a combination of one or more immiscible oils, selected from sesame oil, soybean oil, canola oil, coconut oil, fractionated coconut oil, fish oil, or mineral oil, and about 2-6% w/w of one or more flavor oils, further comprising an organic acid selected from benzoic acid, sorbic acid, malic acid, citric acid and salicylic acid; and a surfactant selected from an anionic surfactant, a zwitterionic surfactant and a non-ionic surfactant or combination thereof, the formulation having a pH between 4.0 and 5.5 and an acrylic contact angle of less than 24°, and wherein the metastable emulsion is a short-lived oil in water dispersion which will start to separate, if left undisturbed, in under 5 minutes.

2. The formulation of claim 1, wherein the acrylic contact angle is between 5° and 18°.

3. A method for preventing denture breath comprising administering to a person in need thereof, an effective amount of a formulation as claimed in claim 1.

4. A method for maintaining fresh breath in the mouth of a dental appliance wearer comprising administering to a person in need thereof, an effective amount of a formulation as claimed in claim 1.

5. A method of cleansing a dental appliance outside the oral cavity comprising maintaining the dental appliance in contact with an alcohol-free dental appliance cleansing formulation for at least about 60 seconds which is a metastable emulsion comprising about 75-90% w/w of an aqueous phase, about 0.5-20% w/w of a water immiscible oily phase, the oily phase having a combination of one or more immiscible oils, selected from sesame oil, soybean oil, canola oil, coconut oil, fractionated coconut oil, fish oil, or mineral oil, and about 2-6% w/w of one or more flavor oils, further comprising an organic acid selected from benzoic acid, sorbic acid, malic acid, citric acid and salicylic acid; and a surfactant selected from an anionic surfactant, a zwitterionic surfactant and a non-ionic surfactant or combination thereof, the formulation having a pH between 4.0 and 5.5 and an acrylic contact angle of less than 24°, wherein the metastable emulsion is a short-lived oil in water dispersion which will start to separate, if left undisturbed, in under 5 minutes, and is dispensed as an aerated foam; and wherein after cleaning, the dental appliance is placed in the oral cavity.

6. The method of claim 2 further comprising the step of rinsing the dental appliance with water, before placing the dental appliance in the oral cavity.

* * * * *